United States Patent [19]
Maisonneuve et al.

[11] Patent Number: 6,107,498

[45] Date of Patent: *Aug. 22, 2000

[54] PROCESS FOR MAKING CARBOXYLIC AMIDES

[75] Inventors: Bernard Maisonneuve, Valley Cottage, N.Y.; Dale Steichen; Ralph Franklin, both of Danbury, Conn.; Kornelis Overkempe, Holten, Netherlands

[73] Assignee: AKZO Nobel N.V., Arnhem, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/837,844

[22] Filed: Apr. 22, 1997

[51] Int. Cl.$^7$ .................................................. C07C 231/00
[52] U.S. Cl. .................. 554/69; 554/35; 554/51; 554/68; 554/70; 564/141; 564/143; 564/139
[58] Field of Search .................................. 554/35, 68, 69, 554/70, 51; 564/141, 139, 143

[56] References Cited

U.S. PATENT DOCUMENTS

| | | |
|---|---|---|
| 2,589,674 | 3/1952 | Cook et al. .................. 200/404.5 |
| 2,963,339 | 12/1960 | Keller ............................................. 8/87 |
| 3,984,335 | 10/1976 | Ciko et al. .................. 510/516 |
| 4,038,294 | 7/1977 | Conner et al. .................. 554/52 |
| 4,059,535 | 11/1977 | De Vault et al. . |
| 4,220,581 | 9/1980 | Cooperman et al. .................. 554/52 |

FOREIGN PATENT DOCUMENTS

| | | |
|---|---|---|
| 35263 | 9/1981 | European Pat. Off. . |
| 328179 | 8/1989 | European Pat. Off. . |
| 336267 | 10/1989 | European Pat. Off. . |
| 580527 | 1/1994 | European Pat. Off. . |
| 1556478 | 2/1969 | France . |
| 2641286 | 6/1977 | Germany . |
| 3437321 | 4/1986 | Germany . |
| 3621345 | 1/1987 | Germany . |
| 3546022 | 6/1987 | Germany . |
| 3626564 | 2/1988 | Germany . |
| 4015849 | 11/1991 | Germany . |
| 4308792 | 4/1994 | Germany . |
| 3060957 | 3/1988 | Japan . |
| 4235148 | 8/1992 | Japan . |
| 6279375 | 10/1994 | Japan . |
| 2160421 | 12/1985 | United Kingdom . |
| 9101295 | 2/1991 | WIPO . |

OTHER PUBLICATIONS

AN 93–339692, Derwent Publications Ltd., London, GB Sep. 24, 1993 (JP 05 246965).
AN 93–239976, Derwent Publications Ltd., London, GB Jun. 29, 1993 (JP 05 163218).
AN 88–115407, Derwent Publications Ltd., London, GB Mar. 17, 1988 (JP 63 060957).
AN 94–354703, Derwent Publications Ltd., London, GB, Oct. 4, 1998, (JP 06 279375).
Chemical Abstract 1993: 603010.

*Primary Examiner*—Shailendra Kumar
*Attorney, Agent, or Firm*—Dilworth & Barrese

[57] ABSTRACT

Methods for producing carboxylic amides involves combining near-stoichiometric amounts of carboxylic acid and amine in a reaction vessel and reacting under pressures greater than atmospheric pressure. Alternatively, an excess of amine is reacted with carboxylic acid at atmospheric pressure to produce a carboxylic amide.

42 Claims, No Drawings

PROCESS FOR MAKING CARBOXYLIC AMIDES

TECHNICAL FIELD

This disclosure relates to the methods for the production of carboxylic amides. Specifically, this disclosure relates to a method wherein a carboxylic acid is reacted with near-stoichiometric amounts of an amine having a boiling point below about 150° C.

BACKGROUND

Production of carboxylic amides has previously been accomplished by the reaction of a carboxylic acid with large excesses of amine. As a result, previous production methods are unfavorable economically and environmentally, requiring either expensive scrubbing and recovery equipment, or release of excess amine into the environment.

For example, GB 2,160,421 discloses a method for preparing stearamidopropyl dimethylamine by reacting 270 parts stearic acid with 100 parts dimethylamino propyl amine, under pressure, at a temperature of 140° C. to 150° C. for three hours. The reaction temperature is then increased to 165° C. to 170° C. and held for one hour completing the reaction. Expensive separation apparatus is suggested when high yields are desirable.

JP 3060957-A discloses the preparation of fatty acid bisamides by reacting fatty acid with a diamine at a molar ratio of 1.85–2.1:1 wherein the reaction temperature is 150–300° C. The reaction is initially conducted under pressure (7–30 kg/cm$^2$) and when the conversion to fatty acid bisamide reaches 85–95 wt % based on the diamine, the reaction system is returned to normal pressure.

JP 6 279 375-A discloses a method for the preparation of carboxylic acid amides that uses pressure but also uses expensive separation equipment for water removal and also uses large excesses of amine.

It would be desirable to produce carboxylic amides without the need for expensive recovery equipment, while removing the necessity of releasing excess amine into the environment.

SUMMARY

The method for producing carboxylic amides described herein involves combining near-stoichiometric amounts of carboxylic acid and amine in a reaction vessel and reacting under pressures greater than atmospheric pressure.

In another embodiment, reaction of carboxylic acid and amine is conducted at atmospheric pressure using a large excess of amine. A bleaching agent is optionally included in the reaction mixture of either embodiment in order to improve the color of the final product.

DETAILED DESCRIPTION OF PREFERRED EMBODIMENTS

The methods described herein produces a carboxylic amide by reaction a carboxylic acid with an amine. Suitable carboxylic acids are those of the formula

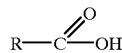

wherein R is an aliphatic or aromatic group, preferably a saturated or unsaturated aliphatic group having from 5 to 24 carbon atoms. Preferably, R is a linear or branched alkyl or alkylene group. R can also be an organic group containing a hetero atom, provided the hetero atom does not interfere with the reaction with the amine. Preferably, the R group is selected from the group consisting of $C_7$–$C_{21}$, branched or linear, saturated or unsaturated alkyl groups. Particularly useful acids include vegetable and animal based fatty acids, including, but not limited to decanoic acid, lauric acid, myristic acid, palmitic acid, stearic acid, oleic acid, erucic acid, behenic acid, coconut acid and tallow acid.

Any primary or secondary amine having a boiling point below about 200° C., preferably below about 160° C. can be employed in the method of the present invention. Preferred amines are of the formula:

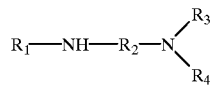

wherein $R_1$ is hydrogen, alkyl or alkenyl, $R_2$ is a bridging group having up to 8 carbon atoms and which may be optionally substituted with hetero atoms or carbonyl groups or combinations thereof, and $R_3$ and $R_4$ can be the same or different and are individually selected from the group consisting of hydrogen and $C_1$–$C_6$ alkyl. A particularly useful amine is 3-dimethylamino propylamine ("DMAPA").

In carrying out the reaction in accordance with a first embodiment, a near-stoichiometric amount of amine is employed. By the term "near-stoichiometric amount" it is meant that less than a 20% excess of amine is added to the reaction mixture. Thus, the molar ratio of amine to carboxylic acid will be in the range of 0.8:1 to 1.2:1. Preferably, no more than about 1.1 moles of amine is present for each mole of acid groups present in the reaction mixture. Most preferably, less than a 5 percent excess of amine is used.

The reactants are added to a reaction vessel in a nitrogen atmosphere and reacted at temperatures in the range of about 40° C. to about 210° C. at pressures ranging from about 0 psi to about 125 psi, preferably about 90 psi to about 105 psi. Overall reaction times are from about 10 hours to about 24 hours.

As the reaction proceeds, the pressure within the reaction vessel will increase due to the formation of water. The reaction vessel is vented to maintain a pressure below about 105 psig. The endpoint in the reaction can be determined by measurement of the residual fatty acid.

In another embodiment an excess of amine is used in the reaction mixture and the reaction of carboxylic acid and amine is carried out at about atmospheric pressure. The reaction is carried out at temperatures in the range of from about 80° C. to about 200° C. Reaction times can range from about 8 to about 30 hours, preferably from about 12 to about 24 hours. Optionally, a bleaching agent can be employed during the reaction. Suitable bleaching agents include hypophosphorous acid. When used, bleaching agent should be added in an amount from about 100 to about 4000 ppm by weight based on the combined amount of the acid and amine, preferably from about 500 to about 3000 ppm.

In this embodiment, an excess of amine is employed. It is preferred that about 5 to about 50 percent excess amine is employed. More preferably, from about 10 to about 40 percent excess amine is employed.

The reaction of amine (e.g., Dimethylaminopropylamine or N,N Dimethylpropane diamine) with carboxylic acid is a condensation reaction, and proceeds with the elimination of water. Water is preferably constantly removed from the reaction zone to allow the reaction to proceed to completion, and achieve a low residual acid content. A nitrogen sparge can be used to assist water removal. While the reaction does not require a catalyst, hypophosphorus acid is optionally used during the reaction to bleach the product and assure a light colored product is made.

The reaction is run at atmospheric pressure with an excess of amine. At the end of the reaction, unreacted amine is stripped from the reaction mix by applying vacuum to the system. The quantity of excess amine required significantly depends on the effectiveness of the overhead reflux system associated with the reactor. Nominally 25%–35% excess amine will be required on a commercial scale. Excess amine is constantly removed from the reaction mass along with the evolved water. Preferably, an overhead "hot" reflux system should separate the water/amine mixture, returning the amine to the reactor, while allowing the water to exit the system to a cold condenser for recovery in a distillate receiver tank.

Another parameter that influences amine losses is the rate of heat-up of the reactor. The reactor is preferably heated quickly to 130° C., and then put into a slow heat-up vs. time ramp mode. At about 140° C. the reaction proceeds rapidly. The temperature is held at this point for approximately two hours before additional ramping further accelerates the reaction rate. The temperature is ramped very slowly, (e.g. 5° C./30 min.), from 140° C. to 180° C. to prevent requiring a higher excess amine level than noted above. A second holding period occurs at 180° C. The reaction phase is over when the residual acid falls below 3%. Then excess amine stripping is initiated.

The distillate from the reaction and amine stripping phases contains all of the excess amine and water generated by the reaction. The amine can advantageously be recycled back to the reactor for economic and environmental purposes. Amine recycle is accomplished by adding the amine/water condensate to the full charge of acid. By the addition of the water/amine mixture to the acid, it is postulated that an amine salt forms which reduces the vapor pressure of the amine to a level where water can be selectively removed. The water (from the prior reaction) is then stripped out by heating the batch to about 150° C. Amine losses from this step are below 0.15% of the total recycle and fresh amine charges (typically the losses are below 0.05% of the fresh and recycle amine charges). The batch is then cooled to 70° C., and a stoichiometric charge of fresh amine is added for the next reaction. The fresh amine charge also accounts for minor amine losses though processing inefficiencies (e.g., low level vent losses or other handling losses).

Significant exotherms occur during the amine addition steps, and the temperature when amine addition starts and amine addition rate are controlled to avoid exceeding critical reaction temperatures prematurely in the batch cycle.

When the resulting product is to be stored for extended period of time (e.g., longer than two weeks), an odor stabilizer optionally can be added to the product. The present fatty acid amides when freshly made have a mild, but not unpleasant odor. For amides derived from fully saturated fatty acids, the possibility of oxidative instability would be considered unlikely by those skilled in the art, and the formation of pyridines not predicted. It is a surprising discovery, therefore, that during storage, these products developed an undesirable "pyridine" like odor. Analysis of product having this characteristic odor revealed the presence of low levels of volatile pyridine derivatives.

It has surprisingly been found that the addition of a antioxidant to freshly made carboxylic amides made from saturated fatty acids provides additional odor stability. Since the carboxylic amides of the present invention oxidize quite readily at very moderate temperatures to produce odor bodies, including pyridines, the incorporation of at least one antioxidant significantly retards the formation of these odor components. The use of a nitrogen blanket in conjunction with an antioxidant further improves odor stability.

When used, an odor stabilizer can be present in an amount from about 50 ppm to about 5000 ppm, preferably about 500 ppm to about 1500 ppm. Examples of antioxidants useful in the context of the present invention include, but are not limited to phenolic antioxidants such as: 3,5-Di-tert-butyl-4-hydroxy toluene (BHT); 3,5-Di-tert-butyl-4-hydroxy anisole (BHA); Corn oil-60%, butylated hydroxytoluene-20%, butylated hydroxyanisole-10%, propyl gallate-6%, citric acid-6%; Octadecyl 3-(3,5-di-tert-butyl-4-hydroxy-phenyl) propionate; and 3,5-Di-tert-butyl-4-hydroxyhydrocinnamic acid, triester with 1,3,5-tris(2-hydroxyethyl)-s-triazine-2,4,6(1H,3H,5H)-trione. Suitable antioxidants include those available under the tradenames. IRGANOX® 1076 and IRGANOX® 3125 from Ciba Geigy Corporation, and under the tradenames TENOX®4 and TENOX®6 from Eastman Chemical Co. Other antioxidants useful herein are readily apparent to one of ordinary skill in the art and can be found, for example, in McCutchen's Functional Materials, 1995 McPublishing Co., N.J., U.S.A., the relevant portions thereof being incorporated herein by reference. In a particularly useful embodiments, butylated hydroxytoluene (BHT) is employed as a odor stabilizer in an amount of between about 500 and 1500 ppm.

The resulting carboxylic amides are useful as surfactants.

The following non-limiting examples illustrate procedures useful in practicing the methods described herein.

EXAMPLE 1

Decanoic acid (670 g) is added to an autoclave and the system is purged with nitrogen. Dimethylaminopropylamine (403 g) is added to a bomb and the bomb is purged with nitrogen. The DMAPA is added to the autoclave by means of nitrogen pressure. The excess pressure in the autoclave is vented and the batch temperature is increased to 175° C. with the autoclave sealed. After 4 hours the decanoic acid content drops to 4–5% and the pressure (approx 80 psi) from the water formed during the reaction is vented gradually over a 45 minute period. The autoclave is then sealed and the temperature is increased to 205° C. and held for 1–2 hours after which the residual pressure is vented once again. With the aid of a slow nitrogen sparge the reaction is then completed (decanoic acid <2%) at 205° C. and atmospheric pressure.

EXAMPLE 2

Decanoic acid (125 lbs) and hypophophorous acid (85 gms) are added to an autoclave. After purging with nitrogen, the acid is heated to 80° C. at atmospheric pressure. DMAPA is blown into the autoclave using nitrogen gas. DMAPA is added at a rate of 1 lb./min to avoid excessive heat build up from the resulting exothermic reaction. A total of 76 lbs DMAPA is added. Temperature is adjusted to be in the range of 95–110° during DMAPA addition.

The temperature is raised to 180° C. and held for four hours. Pressure within the autoclave increases during this period due to the formation of water. The autoclave is vented as necessary to maintain pressure at about 75 psig. The mixture is sampled and tested for residual acid using techniques known to those skilled in the art. When the level of residual acid drops to about 0.25 meq/gm, the autoclave is slowly vented to atmospheric pressure. The temperature is then increased to about 200° C. and reaction is continued until sampling shows that the residual acid is less than about 0.15 meq/gm. The autoclave is then vented again and reaction continues at 205° C. until free acid drops to below about 0.1 meq/gm.

EXAMPLE 3

Into a reaction vessel fitted with thermometer, stirrer, vigreux and distillation column was placed 603.0 grams (3.47 moles) of decanoic acid and 1.08 grams of 50% solution hypophosphorous acid. This was stirred and heated to 50° C. under nitrogen. 427.5 grams (4.16 moles) of dimethylaminopropylamine was added over a period of 10 minutes. The reaction mixture was heated up to 130° C. at a rate of 1° C. per minute. Temperature was raised to 140° C. with a ramp rate of 10° C. per hour and kept at this temperature for about 2 hours. Then, the temperature was raised to 180° C. and held there for one hour. Water and excess amine were stripped off under 29" Hg for 30 minutes, and the distillate collected for recycling.

134.8 grams of the collected distillate (54.9% dimethylaminopropylamine, 45.1% water) were added to 602.5 grams of decanoic acid containing 1.08 grams of hypophosphorous acid. The mixture was heated to 150° C. under $N_2$ to strip off water contained in recycled amine. When most of the water was removed, the mixture was cooled to approximately 70° C. Then, 354.8 grams of fresh dimethylaminopropylamine was added. The reaction was then again conducted as described above.

It should be understood that the foregoing procedure for recycling unreacted amine can be repeated any number of times. Thus, for example, the distillate collected from the second reaction can be used for a third run and so on.

EXAMPLE 4

The odor stabilizing effect of six different antioxidants is evaluated in this Example. The antioxidants evaluated are BHT, TENOX® 4, IRGANOX®1076, BHA, TENOX®6 and IRGANOX®3125. A control sample containing no antioxidant is also evaluated. Two samples of each experiment, one stored under a nitrogen atmosphere and one stored in air, are prepared and evaluated.

The procedure for the sample preparation for this Example is as follows. A freshly prepared sample of the carboxylic amide of Example 3 and the antioxidant (1000 ppm by weight) are weighed into a 30 ml of Wheaton glass serum bottle. The mixture is stirred at room temperature by a magnetic stirred for 10 minutes to obtain a homogeneous solution. The bottle is then sealed by a Teflon-lined rubber septum in the presence of either air or nitrogen. Samples being stored under nitrogen are purged once by nitrogen for another 10 minutes to exclude the air. These samples are then subjected to oven aging at 37° C. for 36 days. Samples are stabilized at 25° C. for 60 minutes before olfactory evaluation.

The control samples (containing no antioxidant) exhibited a strong order whether stored in air or under nitrogen. Each of the antioxidants tested reduced the odor of the carboxylic amide significantly. The samples stored under nitrogen generally exhibited less odor than the corresponding samples stored in air. BHT and TENOX®4 provided the most reduction in odor. While all samples showed some yellowing with time, the samples least affected were those containing BHT and IRGANOX®1076.

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

We claim:
1. A method comprising
   a) combining a carboxylic acid with a near-stoichiometric amount of an amine having a boiling point below about 200° C. in a reaction vessel;
   b) reacting the carboxylic acid and amine at a pressure greater than atmospheric pressure;
   c) reducing pressure in the reaction vessel; and
   d) recovering a carboxylic amide.
2. A method as in claim 1 wherein during step a) the molar ratio of carboxylic acid to amine is in the range of about 0.9:1 to about 1.1:1.
3. A method as in claim 1 wherein during the step of a) less than about 5% of a stoichiometric excess of amine is used.
4. A method as in claim 1 wherein the carboxylic acid is of the formula RCOOH wherein R is an aliphatic or aromatic group.
5. A method as in claim 1 wherein the carboxylic acid is of the formula RCOOH wherein R is a saturated or unsaturated aliphatic group.
6. A method as in claim 1 wherein the carboxylic acid is of the formula RCOOH wherein R is selected from the group consisting of $C_7$ to $C_{21}$ branched or linear, saturated or unsaturated aliphatic groups.
7. A method as in claim 1 wherein the carboxylic acid is selected from the group consisting of vegetable and animal based fatty acids.
8. A method as in claim 1 wherein the carboxylic acid is selected from the group consisting of decanoic acid, lauric acid, myristic acid, palmitic acid, stearic acid, oleic acid, erucic acid, behenic acid, coconut acid and tallow acid.
9. A method as in claim 1 wherein step b) is conducted at a pressure up to about 125 psi.
10. A method as in claim 1 wherein step b) is conducted at a pressure in the range of from about 90 psi to about 105 psi.
11. A method as in claim 1 wherein the amine is of the formula:

$$R_1\text{—}NH\text{—}R_2\text{—}N\begin{cases}R_3\\R_4\end{cases}$$

wherein $R_1$ is hydrogen, alkyl or alkenyl, $R_2$ is a bridging group having up to 8 carbon atoms and may be optionally substituted with hetero atoms or carbonyl groups or combinations thereof and $R_3$ and $R_4$ can be the same or different and are individually selected from the group consisting of hydrogen and $C_1$–$C_6$ alkyl.
12. A method as in claim 1 wherein the amine is dimethylaminopropyl-amine.
13. A method as in claim 1 wherein step a) is conducted in the presence of a bleaching agent.
14. A method as in claim 11 wherein the bleaching agent is hypophosphorous acid.
15. A method comprising:
   (a) reacting a carboxylic acid with from about 5 to about 50 percent of an excess of amine in a reaction vessel at about atmospheric pressure and a temperature in the range from about 130 C to about 150 C;

(b) continuing the reaction at a temperature greater than about 150 C;
(c) distilling off any excess amine and ester;
(d) recovering a carboxylic amide; and
(e) recycling the water and excess amine back to the reaction vessel for use in subsequent reaction.

16. A method as in claim 15 wherein during the step a) the amount of amine employed is in the range of from about 5% to about 50% molar excess.

17. A method as in claim 15 wherein during the step a) the amount of amine employed is in the range of from about 10% to about 40% molar excess.

18. A method as in claim 15 wherein the carboxylic acid is of the formula RCOOH wherein R is an aliphatic or aromatic group.

19. A method as in claim 15 wherein the carboxylic acid is of the formula RCOOH wherein R is a saturated or unsaturated aliphatic group.

20. A method as in claim 15 wherein the carboxylic acid is of the formula RCOOH wherein R is selected from the group consisting of $C_7$ to $C_{21}$ branched or linear, saturated or unsaturated aliphatic groups.

21. A method as in claim 15 wherein the carboxylic acid is selected from the group consisting of vegetable and animal based fatty acids.

22. A method as in claim 15 wherein the carboxylic acid is selected from the group consisting of decanoic acid, lauric acid, myristic acid, palmitic acid, stearic acid, oleic acid, erucic acid, behenic acid, coconut acid and tallow acid.

23. A method as in claim 15 wherein the amine is of the formula:

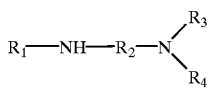

wherein $R_1$ is hydrogen, alkyl or alkenyl, $R_2$ is a bridging group having up to 8 carbon atoms and may be optionally substituted with hetero atoms or carbonyl groups or combinations thereof and $R_3$ and $R_4$ can be the same or different and are individually selected from the group consisting of hydrogen and $C_1$–$C_6$ alkyl.

24. A method as in claim 15 wherein the amine is dimethylaminopropyl-amine.

25. A method as in claim 15 wherein step (b) is continued until the amount of residual free acid is less than about 3% of the starting amount.

26. A method as in claim 15 wherein step a) is conducted in the presence of a bleaching agent.

27. A method as in claim 26 wherein the bleaching agent is hypophosphorous acid.

28. A method as in claim 1 further comprising the step of:
e) adding an effective amount of an odor stabilizer selected from the group consisting of antioxidants to the carboxylic amide.

29. A method as in claim 28 wherein step e) comprises adding from about 50 to about 5000 ppm of an odor stabilizer.

30. A method as in claim 28 wherein step e) comprises adding from about 500 to about 1500 ppm of an odor stabilizer.

31. A method as in claim 28 wherein step e) comprises adding BHT to the carboxylic amide.

32. A method as in claim 28 wherein step e) comprises adding BHA to the carboxylic amide.

33. A method as in claim 15 further comprising the step of:
e) adding an effective amount of an odor stabilizer selected from the group consisting of antioxidants to the carboxylic amide.

34. A method as in claim 33 wherein step e) comprises adding from about 50 to about 5000 ppm of an odor stabilizer.

35. A method as in claim 33 wherein step e) comprises adding from about 500 to about 1500 ppm of an odor stabilizer.

36. A method as in claim 33 wherein step e) comprises adding BHT to the carboxylic amide.

37. A method as in claim 33 wherein step e) comprises adding BHA to the carboxylic amide.

38. A method comprising:
a) providing a carboxylic amide prepared by reacting a saturated carboxylic acid with an amine;
b) combining the carboxylic amide with an effective amount of an odor stabilizer selected from the group consisting of antioxidants.

39. A method as in claim 38 wherein step b) comprises combining from about 50 to about 5000 ppm of an odor stabilizer with the carboxylic amide.

40. A method as in claim 38 wherein step b) comprises combining from about 500 to about 1500 ppm of an odor stabilizer with the carboxylic amide.

41. A method as in claim 38 wherein step b) comprises combining BHT with the carboxylic amide.

42. A method as in claim 38 wherein step b) comprises combining BHA with the carboxylic amide.

* * * * *